US006232126B1

(12) United States Patent
Marshall

(10) Patent No.: US 6,232,126 B1
(45) Date of Patent: May 15, 2001

(54) METHOD FOR OBJECTIVELY ASSESSING THE SEVERITY OF SCARS

(75) Inventor: George Evelyn Marshall, Glasgow (GB)

(73) Assignee: Remes Biomedical Limited, Glasgow (GB)

( * ) Notice: Subject to any disclaimer, the term of this patent is extended or adjusted under 35 U.S.C. 154(b) by 0 days.

(21) Appl. No.: 09/481,257

(22) Filed: Jan. 11, 2000

(30) Foreign Application Priority Data

Jan. 15, 1999 (GB) .................................................. 9900973

(51) Int. Cl.$^7$ ............................. G01N 33/48; C12N 5/08; A61B 5/00; A61B 10/00

(52) U.S. Cl. ........................... 436/63; 436/164; 435/371; 600/306; 600/562

(58) Field of Search ..................... 436/63, 164; 435/371; 600/306, 562

(56) References Cited

PUBLICATIONS

"Rating the Resolving Hypertrophic Scar: Comparison of the Vancouver Scar Scale and Scar Volume" Nedelec et al, 2000.*

* cited by examiner

Primary Examiner—Lyle A. Alexander
Assistant Examiner—Monique T. Cole
(74) Attorney, Agent, or Firm—Iandiorio & Teska

(57) ABSTRACT

A method for objectively assessing the severity of scars, which method comprises:

(i) classifying cell nuclei in scar tissue into different types of nuclei such that one of the types is elongated nuclei which is different from other nuclei in that the elongated nuclei has a ratio of length to breadth which exceeds a predetermined number;

(ii) measuring the angle that the longest axis of the elongated nuclei makes with the surface of tissue surrounding the scar; and (iii) ranking the severity of the scar on the basis of the degree of alignment of the elongated nuclei with the surface of the tissue surrounding the scar.

11 Claims, 3 Drawing Sheets

High power of scar tissue showing three classes of
nuclear morphology: small (A), elongated (B) and large (C).

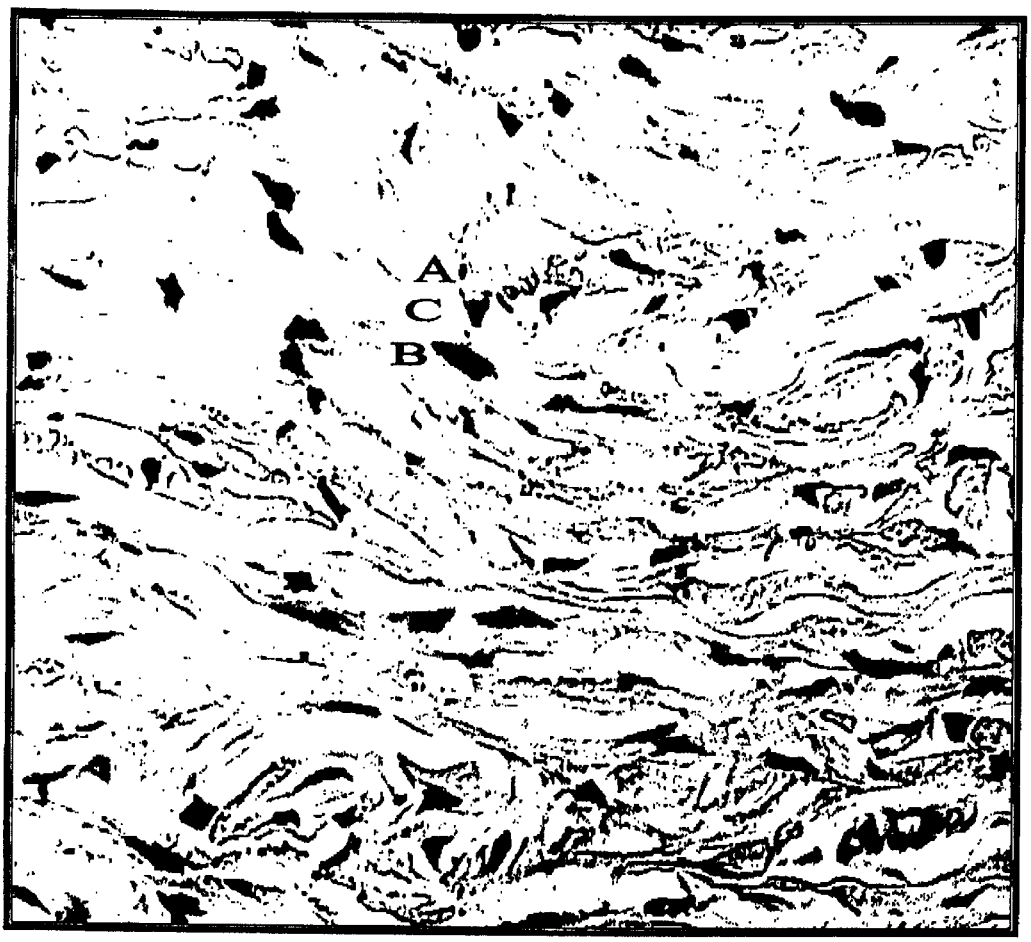
Fig 1: High power of scar tissue showing three classes of nuclear morphology: small (A), elongated (B) and large (C).

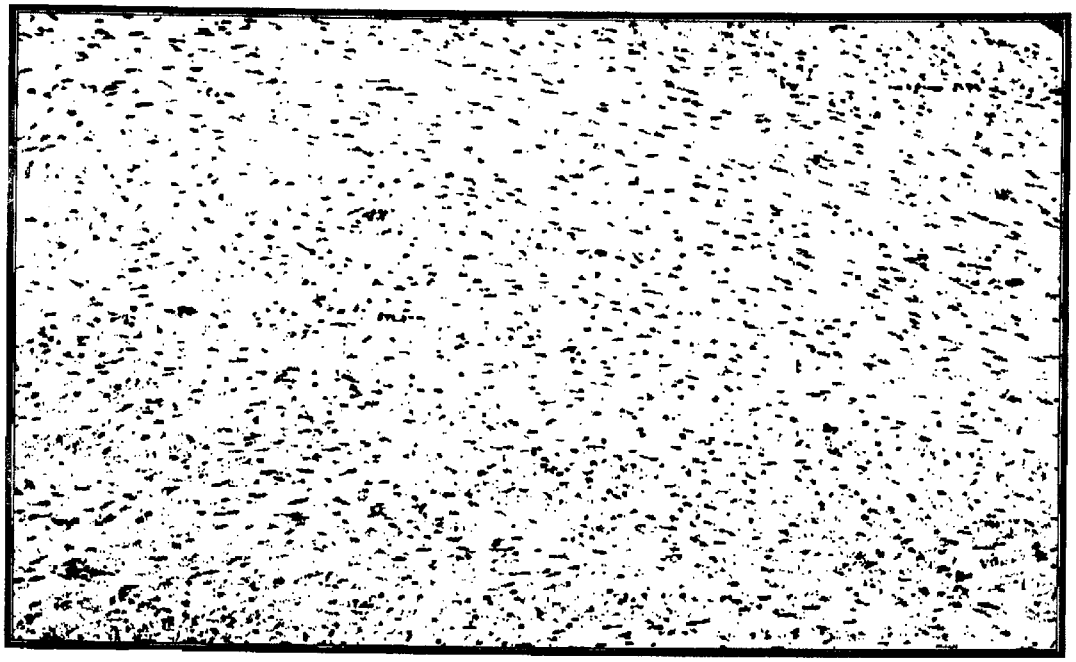
Fig 2: Typical image of scar tissue used for image analysis.
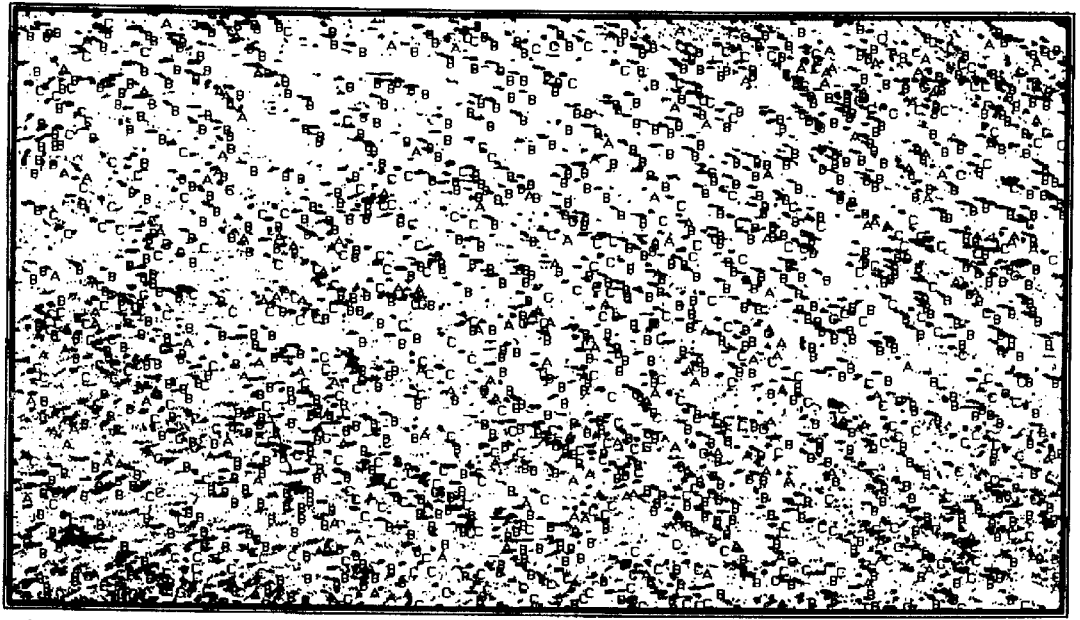
Fig 3: Computerized analysis of above image (A- small nuclei, B – elongated nuclei, C – large nuclei).

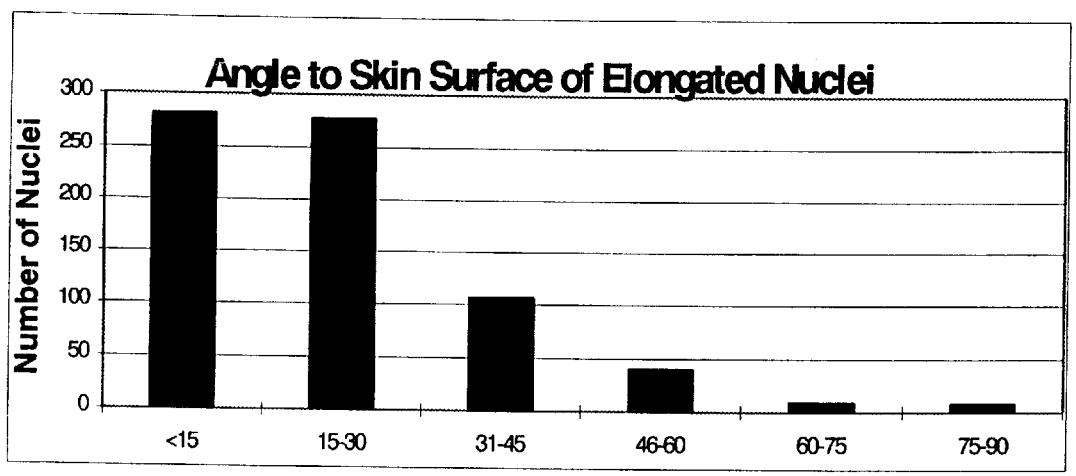
Fig 4: Graph of angles that elongated nuclei make with the surface of skin ($0°$ = parallel to skin, $90°$ = perpendicular to skin)

METHOD FOR OBJECTIVELY ASSESSING THE SEVERITY OF SCARS

This invention relates to a method for objectively assessing the severity of scars. The scars may be in skin or other tissues such for example as blood vessels, kidneys, liver or other tissue organs.

Scarring is clearly undesirable, both from an aesthetic point of view where the scaring is visible, and from a loss of mobility point of view. Scarring that arises from trauma, especially from burns, can cause serious loss of mobility such for example as to the opening and closing of a person's mouth, eyelids and use of limbs. Several potential therapeutic agents have been developed in recent years but their general availability to physicians has been delayed by a lack of an objective assessment as to their effectiveness.

Originally, attempts to assess the severity of scars in skin was by visual inspection of the skin surface. These attempts proved unreliable since they are influenced by a wide variety of factors such for example as the brightness of ambient lighting, and the angle at which light strikes the skin. The visual inspection of the skin surface has been replaced with visual assessment of histological sections of scar tissue by a number of trained histologists, who grade the scarring as mild, moderate, severe or very severe. Even this method of visual assessment by a number of trained histologists is not satisfactory as the grading is not reproducible, and the results obtained from the histologists lack consistency.

It is an aim of the present invention to obviate or reduce the above mentioned problems.

Accordingly, in one non-limiting embodiment of the present invention, there is provided a method for objectively assessing the severity of scars, which method comprises:

(i) classifying cell nuclei in scar tissue into different types of nuclei such that one of the types is elongated nuclei which is different from other nuclei in that the elongated nuclei has a ratio of length to breadth which exceeds a predetermined number;

(ii) measuring the angle that the longest axis of the elongated nuclei makes with the surface of tissue surrounding the scar; and (iii) ranking the severity of the scar on the basis of the degree of alignment of the elongated nuclei with the surface of the tissue surrounding the scar.

The method of the present invention enables the severity of the scars to be objectively assessed since it relies upon features which can be physically measured, and therefore stored and reproduced. This is considerable improvement on the above mentioned inconsistent views of trained histologists.

The method may be one in which the scar tissue is classified into small nuclei having less than a predetermined area, large nuclei having more than a predetermined area, and the elongated nuclei. The elongated nuclei will usually be larger than the large nuclei.

The predetermined area may be greater than 5 $\mu m^2$.

The predetermined number may be 1.7.

The method of the present invention may be one in which the angle is measured and expressed as an angle between 0°–90°, with 0° being parallel to the surface of the tissue surrounding the scar and 90° being perpendicular to the surface of the tissue surrounding the scar.

The method may be one in which the scar tissue is sectioned into sections which are of such a size as to produce sufficient contrast between the different types of nuclei, and which minimise overlap between the different types of nuclei. Preferably, the scar tissue is sectioned into sections which are 3–4 $\mu m$ wide.

The scar tissue is preferably sectioned by microtome sectioning.

The method of the invention may advantageously be one in which the sectioned scar tissue is treated to obtain histological staining of the cell nuclei, in which the histologically stained cell nuclei is filmed on a video camera and the results stored on a computer as an image file, and in which a plurality of the image files are then analysed by computer analysis to effect the classification of the nuclei, the measurement of the angle that the longest axis of the elongated nuclei makes with the surface of the tissue surrounding the scar, and the ranking of the severity of the scar.

Preferably, the computer analysis is printed out as a hard copy graph.

The method may be one in which the number of elongated nuclei that are less than the predetermined angle to the surface of the tissue surrounding the scar is divided by the total number of elongated nuclei, and the result is expressed as a ratio or percentage, with the scars being arranged in rank order of severity by organizing the ratios or percentages in ascending order.

In order to facilitate a full understanding of the present invention, reference will now be made to the following Example.

EXAMPLE

The severity of scars in skin was effected by making the following steps.

1. Removing scar tissue.
2. Formalin fixing the scar tissue, and processing it through to wax.
3. Microtome sectioning of 3 $\mu m$ paraffin sections.
4. Histologically staining cell nuclei.
5. Examining the histologically stained cell nuclei under a light microscope, grabbing a low power view of the scar by a video camera, and saving the low power view on computer as an image file.
6. Analysing image files using appropriate image analysis software. During the analysis, selecting elongated nuclei which were differentiated from the other nuclei in that the ratio of length to breadth in the elongated nuclei exceeded a predetermined number.
7. Measuring the angle that the longest axis of each elongated nucleus makes with the surface of the skin, and expressing this angle as an angle between 0°–90°, with 0° being parallel to the skin surface and 90° being perpendicular to the skin surface.
8. Transferring all data to an Excel sheet, processing the data and expressing it in the form of graphs.
9. Dividing the number of elongated nuclei that are less than a predetermined angle to the surface of the skin by the total number of elongated nuclei, and expressing the result as a ratio or percentage. Then arranging the scars in rank order of severity by organizing the ratios or percentages into an ascending order.
10. Backing up all images and Excel workbooks in order to provide an audit trial.

Reference will now be made to the following drawings which are given by way of example only and in which:

FIG. 1 is a high power view of scar tissue obtained in the Example referred to above;

FIG. 2 is a typical image of scar tissue;

FIG. 3 is a computerised analysis of the typical image shown in FIG. 2; and

FIG. 4 is a graph of angles that elongated nuclei make with the surface of the skin.

Referring to FIG. 1, there is shown a high power view of scar tissue, showing three classes of nuclei morphology, namely small nuclei which are marked by the letter A, elongated nuclei which are marked by the letter B, and large nuclei which are marked by the letter C.

FIG. 2 shows a typical image of scar tissue used for the image analysis referred to in the above Example.

FIG. 3 shows a computerised analysis of the image shown in FIG. 2. Small nuclei are marked by the letter A, elongated nuclei are marked by the letter B, and large nuclei are marked by the letter C.

FIG. 4 shows a graph of angles that the elongated nuclei make with the surface of the skin, with 0° being parallel to the surface of the skin and 90° being perpendicular to the surface of the skin.

It is to be appreciated that the Example and the drawings given above have been given by way of example only and that modifications may be effected. Thus for example, the scars can be in tissue other than skin so that the scars may be in blood vessels, kidneys, liver or other tissue organs. The scars will usually be in humans but they may also be in animals.

What is claimed is:

1. A method for objectively assessing the severity of scars, which method comprises:
   (i) classifying cell nuclei in scar tissue into different types of nuclei such that one of the types is elongated nuclei which is different from other nuclei in that the elongated nuclei has a ratio of length to breadth which exceeds a predetermined number;
   (ii) measuring the angle that the longest axis of the elongated nuclei makes with the surface of tissue surrounding the scar; and
   (iii) ranking the severity of the scar on the basis of the degree of alignment of the elongated nuclei with the surface of the tissue surrounding the scar.

2. A method according to claim 1 in which the scar tissue is classified into small nuclei having less than a predetermined area, large nuclei having more than a predetermined area, and the elongated nuclei.

3. A method according to claim 2 in which the predetermined area is greater than 5 $\mu m^2$.

4. A method according to claim 1 in which the predetermined number is 1.7.

5. A method according to claim 1 in which the angle is measured and expressed as an angle between 0°–90°, with 0° being parallel to the surface of the tissue surrounding the scar and 90° being perpendicular to the surface of the tissue surrounding the scar.

6. A method according to claim 1 in which the scar tissue is sectioned into sections which are of such a size as to produce sufficient contrast between the different types of nuclei, and which minimise overlap between the different types of nuclei.

7. A method according to claim 6 in which the scar tissue is sectioned into sections which are 3–4 $\mu m$ wide.

8. A method according to claim 6 in which the scar tissue is sectioned by microtome sectioning.

9. A method according to claim 6 in which the sectioned scar tissue is treated to obtain histological staining of the cell nuclei, in which the histological stained cell nuclei is filmed on a video camera and the results stored on a computer as an image file, and in which a plurality of the image files are then analysed by computer analysis to effect the classification of the nuclei, the measurement of the angle that the longest axis of the elongated nuclei makes with the surface of the tissue surrounding the scar, and the ranking of the severity of the scar.

10. A method according to claim 9 in which the computer analysis is printed out as a hard copy graph.

11. A method according to claim 1 in which the number of elongated nuclei that are less than the predetermined angle to the surface of the tissue surrounding the scar is divided by the total number of elongated nuclei, and the result is expressed as a ratio or percentage, with scars being arranged in rank order of severity by organizing the ratios or percentages in an ascending order.

* * * * *